United States Patent [19]

Knapp et al.

[11] Patent Number: 5,035,776
[45] Date of Patent: Jul. 30, 1991

[54] LOW ENERGY EXTRACTIVE DISTILLATION PROCESS FOR PRODUCING ANHYDROUS ETHANOL

[75] Inventors: Jeffrey P. Knapp, Newark, Del.; Michael F. Doherty, Montague, Me.

[73] Assignee: University of Massachusetts, Amherst, Mass.

[21] Appl. No.: 502,112

[22] Filed: Mar. 29, 1990

[51] Int. Cl.⁵ .............................................. B01D 3/40
[52] U.S. Cl. ....................................... 203/19; 203/23; 203/26; 203/27; 203/75; 203/77; 203/78; 203/80; 203/82; 203/84; 203/DIG. 8; 203/DIG. 9; 203/DIG. 13; 426/494; 435/161; 568/916
[58] Field of Search ....................... 203/19, 25, 26, 80, 203/DIG. 8, DIG. 13, 64, 23, DIG. 16, DIG. 9, 27, 75, 77, 78, 82, 84; 568/916; 435/161; 426/494

[56] References Cited

U.S. PATENT DOCUMENTS

| | | | |
|---|---|---|---|
| 1,702,495 | 2/1929 | Clapp | 203/19 |
| 1,822,454 | 9/1931 | Ricard et al. | 203/19 |
| 1,860,554 | 5/1932 | Ricard et al. | 203/19 |
| 3,960,672 | 6/1976 | Ester, deceased et al. | 203/37 |
| 3,990,952 | 11/1976 | Katzen et al. | 203/33 |
| 4,081,354 | 3/1978 | Christman | 208/235 |
| 4,161,429 | 7/1979 | Baiel et al. | 203/18 |
| 4,217,178 | 8/1980 | Katzen et al. | 203/19 |
| 4,256,541 | 3/1981 | Muller et al. | 203/19 |
| 4,294,664 | 10/1981 | Anthony | 203/19 |
| 4,305,790 | 12/1981 | Kramer, Sr. | 203/19 |
| 4,306,942 | 12/1981 | Brush et al. | 203/19 |
| 4,366,032 | 12/1982 | Mikitenko et al. | 203/18 |
| 4,372,822 | 2/1983 | Muller et al. | 203/19 |
| 4,382,843 | 5/1983 | Black | 203/19 |
| 4,400,241 | 8/1983 | Braithwaite | 203/DIG. 13 |
| 4,422,903 | 12/1983 | Messick et al. | 203/19 |
| 4,428,798 | 1/1984 | Zudkevitch et al. | 203/19 |
| 4,455,198 | 6/1984 | Zudkevitch et al. | 203/19 |
| 4,492,637 | 1/1985 | Tao et al. | 210/711 |
| 4,503,079 | 3/1985 | King et al. | 426/494 |
| 4,541,897 | 9/1985 | Sommer et al. | 203/19 |
| 4,559,109 | 12/1985 | Lee et al. | 203/19 |
| 4,626,321 | 12/1986 | Grethlein et al. | 203/26 |
| 4,631,115 | 12/1986 | Berg et al. | 203/19 |
| 4,645,567 | 2/1987 | Akabane et al. | 203/DIG. 8 |
| 4,654,123 | 3/1987 | Berg et al. | 203/19 |
| 4,692,218 | 9/1987 | Houben et al. | 203/19 |

FOREIGN PATENT DOCUMENTS

| | | | |
|---|---|---|---|
| 8802649 | 4/1988 | European Pat. Off. | 203/19 |
| 0200302 | 4/1983 | Fed. Rep. of Germany | 203/19 |

OTHER PUBLICATIONS

"Multi-Effect Extractive Distillation for Separating Aqueous Azeotropes" by S. Lynn and D. N. Hanson, Industrial and Engineering Chemistry, Process Design and Development, vol. 25, pp. 936-941.

*Primary Examiner*—Virginia Manoharan
*Attorney, Agent, or Firm*—Welsh & Katz, Ltd.

[57] ABSTRACT

A thermally-integrated extractive distillation process for recovering anhydrous ethanol from fermentation or synthetic feedstocks has a distillation train of four columns. Two columns are preconcentrators operated in parallel. The remaining columns are an extractive distillation dehydrating tower, and an entrainer-recovery column. The two preconcentrators and the dehydrating tower are operated at three successively increasing pressures so that the condensing vapors of the overhead product of the dehydrating tower supply the necessary heat to the reboiler of the intermediate-pressure preconcentrator. The overhead vapors of this preconcentrator are, in turn, used to supply the required heat to the reboiler of the lowest-pressure preconcentrator. The bottom product from each preconcentrator is used to preheat the dilute feed. Additional energy savings are accomplished by the appropriate heat exchange between the various feeds, overheads, and bottoms.

24 Claims, 2 Drawing Sheets

LOW ENERGY EXTRACTIVE DISTILLATION PROCESS FOR PRODUCING ANHYDROUS ETHANOL

BACKGROUND OF THE INVENTION

This application relates to the production of anhydrous ethanol, and more particularly to the production of anhydrous ethanol by extractive distillation.

Ethanol is generally produced either synthetically by the hydration of ethylene or by the fermentation of sugar, corn, or other biomass sources. It can be widely used as a chemical intermediate, solvent, and motor-fuel additive.

The Environmental Protection Agency mandated phase-out of tetra-ethyl lead from gasoline and a desire to decrease the dependence on imported crude oil has led to an increased interest in ethanol as a gasoline octane booster and gasoline extender. Furthermore, a recent study indicates that fermentation-ethanol-based ethyl tert-butyl ether has superior properties to the most commonly used oxygenate, methyl tert-butyl ether. The 1986 U.S. production of fuel ethanol from corn was about 600 million gallons, up from nearly zero in 1978, and it is estimated that an additional 5-6 billion gallons per year of ethanol could be produced from the surplus corn grown in the U.S. Because gasohol, gasoline with 10 volume percent ethanol, receives partial exemption from federal excise taxes, at this time ethanol is almost exclusively blended with gasoline in this proportion. Gasohol requires anhydrous (99.5 to 99.8 vol%) ethanol to prevent phase separation of water from gasoline in fuel tanks.

Although other methods exist, the conventional method for producing anhydrous ethanol from dilute fermentation beers or synthetic crude alcohol is by one of two different types of distillation, heterogeneous azeotropic distillation or extractive distillation. Both methods typically use three distillation columns operating at essentially atmospheric pressure with each column heated separately by steam and cooled by cooling water. The first column in each sequence is a preconcentrator often called a stripper-rectifier. The stripping and rectifying may also be accomplished in separate columns. In the first column, a dilute feed containing, for example, 6 to 10 wt% ethanol is concentrated to roughly 85-95 wt% ethanol in the overhead product with the excess water leaving in the bottom stream. The overhead vapor is condensed and part of it is returned as reflux, while the rest is fed to the second or dehydrating tower. At this point, the two distillation methods differ. Heterogeneous azeotropic distillation employs an azeotropic entrainer such as pentane, benzene, heptane, or cyclohexane that forms a heterogeneous ternary azeotrope with ethanol and water. The desired anhydrous ethanol is recovered as the bottom product from this tower. The heterogeneous ternary azeotrope is removed as the overhead product. Upon condensation, the azeotrope phase separates into two liquid phases. The organic phase is used for reflux and the aqueous phase is sent to the third column.

In contrast, extractive distillation uses a high-boiling, completely miscible, nonazeotrope-forming entrainer such as ethylene glycol. The entrainer is used as the upper feed while the preconcentrated ethanol stream becomes the lower feed. The desired anhydrous ethanol product is removed as the distillate and the remaining water and the entrainer exit for the third column via the bottom stream.

The third column in both sequences is used to recover the azeotropic agent or extractive entrainer for recycling to the dehydrating column.

A frequently cited drawback to the production of fuel-grade anhydrous ethanol from renewable grain and biomass sources is that the traditional purification of ethanol by distillation is energy intensive, consuming 50 to 80% of the energy used in typical ethanol-producing fermentation processes. Consequently, a number of energy saving techniques have been proposed over the years, such as methods employing heat pumps, multiple pressure levels for thermal energy re-use, multiple effects, feed preheating schemes, and non-distillation purification processes.

Energy conservation in the heterogeneous azeotropic distillation process has received much more attention in the literature than energy conservation in the extractive distillation process. For example, U.S. Pat. Nos. 1,822,454 and 1,860,544 proposes operating the preconcentrator at a higher pressure than the azeotropic column so that the preconcentrator's condensing overhead vapors could be used to heat the azeotropic column. They also use the bottom stream from the preconcentrator to preheat dilute feed. More recently, U.S. Pat. No. 4,217,178 teaches the use of the condensing overhead vapors of a pressurized preconcentrator to heat both the azeotropic column and the azeotropic-agent recovery column along with a unique feed preheating scheme for additional energy savings. U.S. Pat. No. 4,161,429 teaches increasing the pressure of the azeotropic column relative to the other columns in the sequence for energy conservation. U.S. Pat. No. 4,372,822 teaches pressurizing both the heterogeneous azeotropic column and the azeotropic-agent recovery column so that their condensing overhead vapors could be used to supply the heat needed by the preconcentrator. An energy efficient heterogeneous azeotropic distillation process taught in U.S. Pat. No. 4,422,903 which reduces the steam consumption to the order of 14 to 18 pounds per U.S. gallon of anhydrous ethanol product (11,760-15,120 Btu/gal), depending on the ethanol concentration of the original feed. To accomplish this, the preconcentrator is divided into two effects operating in parallel and three pressure levels are used. The azeotropic and azeotropic-agentrecovery columns operate at the highest pressure level. Their overhead vapors are condensed by reboiling the intermediate-pressure preconcentrator. The condensing overhead vapors of the intermediate-pressure preconcentrator supply the necessary heat to the reboiler of the low-pressure preconcentrator. Additional energy is saved by preheating the dilute feed first with the overhead vapors of the low-pressure preconcentrator and then with the bottom product from both preconcentrators.

In contrast, there is only one study in the literature on thermally-integrated extractive distillation for purifying ethanol. Lynn and Hanson (Ind. Eng. Chem. Proc. Des. Dev., 25, 936, 1986) propose two multi-effect, multiple-pressure-level extractive distillation processes. Both sequences employ two vacuum columns, a vapor feed to the extractive column, and feed preheating by heat exchange with the bottom streams of the preconcentrators. The first alternative uses two preconcentrators operating in parallel. The pressures of one of the preconcentrators and the extractive column are increased so that their condensing overhead vapors reboil the low-pressure preconcentrator. The second alternative splits the preconcentrating step between three effects operating in parallel. The pressures of the intermediate-pressure preconcentrator and the extractive column are sufficiently high that their condensing overhead vapors can be used to supply the required heat to the low-pressure preconcentrator. The pressure of the third preconcentrator is increased enough that its condensing overhead vapors can be used to reboil the intermediate-pressure preconcentrator.

Though the heterogeneous azeotropic distillation process is more commonly used, it does have some serious disadvantages. It is well known in the chemical industry that heterogeneous azeotropic distillations are exceptionally difficult processes to operate and control. Azeotropic columns often behave erratically, and within certain parameters ranges, these columns appear to exhibit multiple steady-states.

SUMMARY OF THE INVENTION

An object of the subject invention is the provision of an improved energy-efficient extractive distillation process for producing various grades of anhydrous ethanol from fermentation or synthetic feedstocks.

A further object of the subject invention is the production of anhydrous ethanol by a distillation process which is not subject to the operability and controllability problems associated with heterogeneous azeotropic distillation.

The above and other objectives are achieved in accordance with the subject invention wherein the distillation columns are operated in a specific sequence at different pressures so that the condensers of the higher pressure columns can supply the heat needed by the reboiler of the lower pressure columns. As much of the required heating and cooling of feeds, distillates, and bottoms as possible is performed by heat exchange with other feed, distillate, or bottoms streams. More specifically, the preferred embodiment of the invention consists of four columns: two preconcentrators operated in parallel, an extractive distillation dehydrating tower, and an entrainer recovery-column. Substantial energy savings are achieved by operating the two preconcentrators and the dehydrating tower at three successively increasing pressures so that the condensing vapors of the overhead product of the dehydrating tower supply the necessary heat to the reboiler of the intermediate-pressure preconcentrator. The overhead vapors of this preconcentrator are, in turn, used to supply the required heat to the reboiler of the lowest-pressure preconcentrator. Optionally, the pressure of the entrainer-recovery column can be increased so that the column's condensing overhead vapors help supply heat to the low-pressure preconcentrator. Additional energy savings are accomplished by using the bottom product from each preconcentrator to preheat the dilute feed. In another embodiment, a three-column sequence employing only one preconcentrator is used.

Other objects and features of the subject invention will be apparent upon consideration of the accompanying drawings and detailed description wherein:

DETAILED DESCRIPTION OF THE DRAWING

Figure 1:
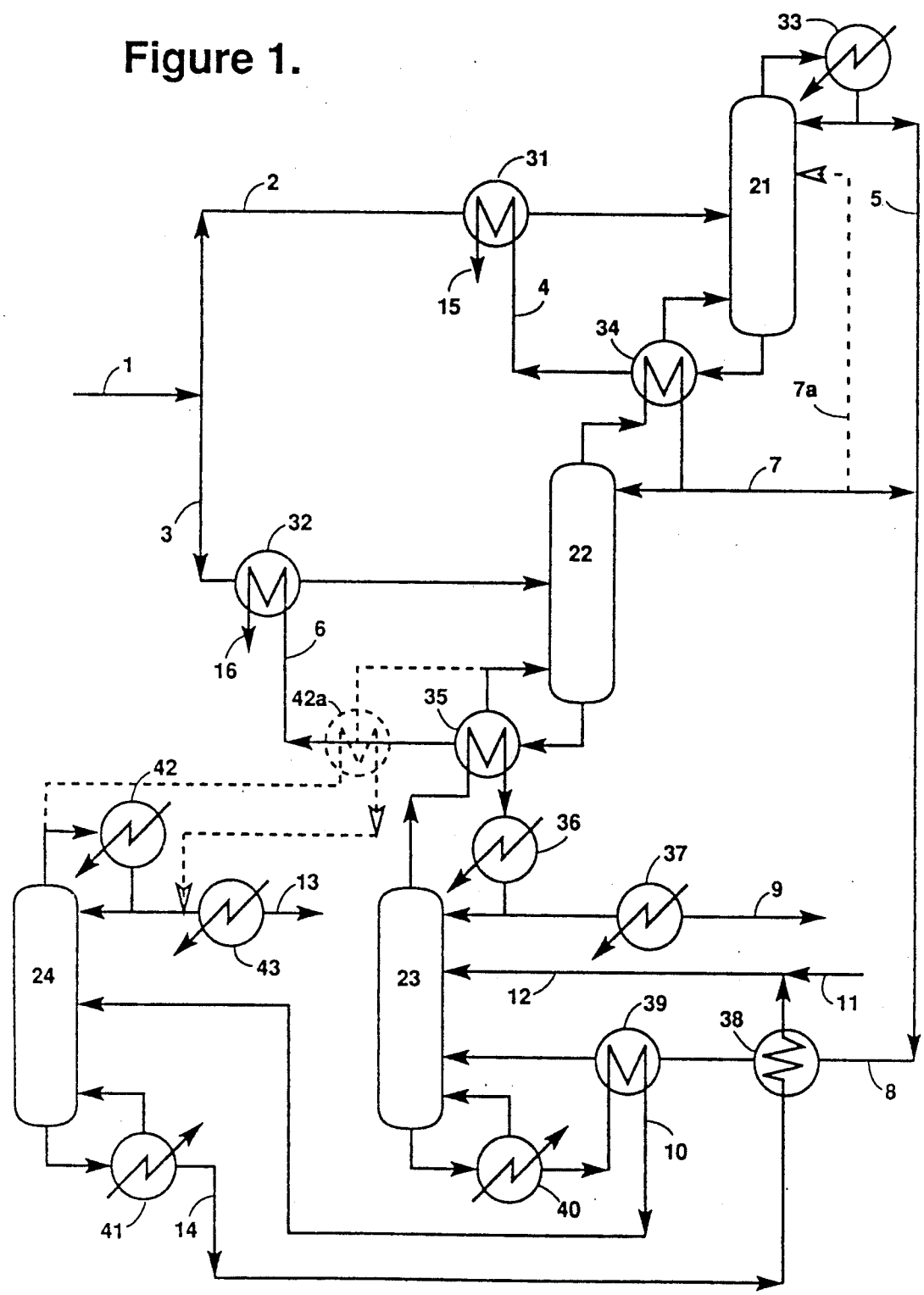
FIG. 1 is a schematic diagram of the process of the subject invention.

Although any suitable fermented or synthetic feed and any feasible extractive entrainer can be used in practicing this invention, the distillation sequence shown schematically in FIG. 1 and described in the example below is for a dilute fermentation beer feedstock and uses ethylene glycol as the extractive agent. In particular, the process described purifies a 2.4–4.2 mol% (6–10 wt%) ethanol feed into 99.8 mol% (99.9 wt%) anhydrous ethanol using the preferred four-column, three-pressure-level version of the invention. Other feedstocks and product compositions may be used, and different fractional recoveries may be experienced.

As shown in the figure, in the preferred embodiment of the subject invention, the fermentation beer enters the separation process at a temperature of 95–100° F. through line 1. The beer feed 1 is divided into two unequal parts to become the feedstreams to the two preconcentrators, or stripper-rectifiers or distillation columns 21 and 22 which operate in parallel. Approximately 50–60% of the total feed on a molar basis passes through line 3 to become the feed to the high-pressure preconcentrator 22. The remaining portion of the total feed flows through line 2 to become the feed to the low-pressure preconcentrator 21.

Stream 2 is heated as hot as possible in heat exchanger 31 by the bottom stream 4 from tower 21 and is then fed to preconcentrator 21. Preconcentrator 21 separates the feed into a distillate of 70–84 mol% ethanol and a bottom stream containing less than 0.10 mol% ethanol. The overhead vapors from tower 21 are condensed in the water-cooled total condenser 33. Part of the condensate is returned as reflux and the rest leaves as distillate stream 5. The bottom stream 4, comprised mainly of water, is first cooled in exchanger 31 by the cold feed stream 2 and then leaves the ethanol purification process as stream 15. Heat is supplied to the low-pressure preconcentrator 21 by condensing the overhead vapors from the high-pressure preconcentrator 22 in condenser-reboiler 34.

Stream 3, the larger fraction of the original feed, is pressurized, heated as hot as possible in exchanger 32 by the bottom stream 6 from column 22, and then is fed to preconcentrator 22.

Preconcentrator 22 performs the same separation as tower 21 but at a higher pressure. The pressure of column 22 is chosen such that its overhead vapors condense at a higher temperature than the boiling temperature of the bottom stream of the low-pressure preconcentrator 21. The overhead vapors from preconcentrator 22 are totally condensed in condenser-reboiler 34 by reboiling preconcentrator 21. Part of the condensate is returned to 22 as reflux while the rest leaves as the distillate stream 7. In an alternative, distillation column 22 could operate as a bear stripper with its condensed overhead stream 7 becoming a second feed via line 7a, as shown in phantom, to the first distillation column 21. The bottom stream 6, comprised mainly of water, is cooled in exchanger 32 by the cold feed stream 3 and then leaves the ethanol purification process as stream 16. The heat required by the high-pressure preconcentrator 22 is supplied by condensing the overhead vapors of the pressurized extractive distillation column 23 in condenser-reboiler 35.

The two condensed distillate streams 5 and 7 from the preconcentrators 21 and 22 are pressurized and mixed to form stream 8. Stream 8 is heated as hot as possible first by the entrainer-recycle stream 14 in exchanger 38 and then by the bottom stream 10 of column 23 in exchanger 39. Other feed preheating/cooling schemes exist for streams 8, 10, 12, and may be used, but the one presented here was found to be the optimal. Finally, the now partially vaporized stream B is fed to the pressurized column 23. Tower 23 is the extractive distillation dehydrating column, and is a double-feed column. The lower feed is the preconcentrated ethanol stream 8, while the upper feed 12 is nearly pure extractive entrainer--ethylene glycol in this particular example. The entrainer-recycle stream 14 from the bottom of column 24 is pressurized, cooled in exchanger 38, and then mixed, as needed, with a small amount of pure entrainer entering through the entrainer make-up stream 11 to become the upper feed 12. Extractive column 23 produces a distillate of the desired anhydrous ethanol concentration. 99.8 mol% is obtained for this example, though purities as high as 99.998 mol% have also been obtained. A bottom stream containing less than 0.02 mol% ethanol is also obtained. The extractive column is the highest pressure column in the sequence. Its pressure is chosen so that the temperature of its condensing overhead vapors is higher than the boiling temperature of the bottom stream of column 22. The overhead vapors from column 23 are condensed in condenserreboiler 35 by reboiling preconcentrator 22. The temperature of the upper feed 12 is set by choosing the heat load on exchanger 38 so that the required condenser duty of the extractive column 23 is as close as possible to the amount of heat necessary to reboil preconcentrator 22. Any necessary additional condensing/cooling of the overhead vapors of column 23 is accomplished in the water-cooled condenser 36. Part of the condensed overhead is returned to 23 as reflux and the rest becomes the desired anhydrous ethanol product stream 9 after being cooled to the storage temperature in product cooler 37. The energy necessary to operate the extractive column 23 is supplied by the steam-driven reboiler 40.

After leaving the bottom of the extractive column 23, stream 10 is cooled as much as possible in exchanger 39 by preheating stream 8. Stream 10 is then flashed to the pressure of column 24 and becomes the feed to 24. Column 24 is the entrainer-recovery column. The overhead vapors from tower 24 condense in the water-cooled condenser 42. Part of the condensed overhead is used as reflux. The rest, stream 13, passes through the water-cooled product cooler 43 and then leaves the process. Essentially all of the water and ethanol in the feed 10 leave in the distillate 13. The bottom stream 14 is high-purity entrainer (ethylene glycol in this example). After leaving the recovery column 24, stream 14, the entrainer-recycle stream is pressurized, cooled in exchanger 38, and then becomes the upper feed to the extractive column 23. If stream 14 contains more than a trace amount of water, it becomes impossible to achieve the desired ethanol purity in the extractive column 23. Also, as mentioned above, the target temperature of stream 14 leaving exchanger 38 is set so that the condenser duty of column 23 is close to the reboiler duty of tower 22. Heat is supplied to the recovery column 24 by a steam-driven reboiler 41. In an alternative, tower 24 could be pressurized and its overhead vapors could be directed too condenser-reboiler 42a, as shown in phantom, to heat the second distillation column 22.

There are several features of fermentation ethanol distillation processes not set forth in the figure, but known in the art and assumed to be included when practicing this invention. For instance, it is customary to include means as known in the art for removing the dissolved carbon dioxide, the fuel oils, and the aldehydes and other light components in the fermented beer feed. Also, auxiliary heat exchangers may be desired to start up and help operate and control the process. The equipment needed to adjust the pressure of the various streams is not shown in the figure but may be of standard design.

From the above discussion, it can be seen that the invention achieves a substantial reduction in energy consumption by the maximum use of hot and/or condensing process streams for the heating/boiling of other process streams. In fact, by using this version of the invention, the energy required to produce 99.8 mol% ethanol from a 4.2 mol% ethanol feed can be reduced to about 7640 Btu/gal of anhydrous ethanol. This is a savings of 65% over an optimized, non-thermally-integrated extractive distillation process. The methods used to accomplish this energy savings can be summarized by:

(1) dividing the task of concentrating the dilute feed between two preconcentrators or stripper-rectifiers 21 and 22 which operate in parallel;

(2) operating preconcentrator 22 at an elevated pressure chosen such that the condensing overhead vapors of tower 22 are hot enough to reboil preconcentrator 21;

(3) using the bottom streams of each preconcentrator to preheat the feeds., i.e., using stream 4 to heat stream 2 in exchanger 31 and using stream 6 to heat stream 3 in exchanger 32;

(4) operating the extractive distillation dehydrating column 23 at an elevated pressure so chosen that the condensing overhead vapors of tower 23 are hot enough to reboil the high-pressure preconcentrator 22;

(5) adjusting the temperature of the upper feed 12 to the extractive column 23 by means of the temperature of the entrainer-recycle stream 14 leaving the feed preheater 38 so that the condenser duty of the extractive column 23 is as close as possible to the reboiler duty of the high-pressure preconcentrator 22; and (6) preheating the lower feed 8 to the extractive column 23 as much as possible by stream 10, the bottom stream from 23 and the feed to 24, in heat exchanger 39 and by the entrainer-recycle stream 14 in exchanger 38.

Thus, the only heat input to the process under normal operating conditions is the steam supplied to the reboilers of the extractive column 23 and the recovery column 24.

The only restriction placed on the column pressures is that they be sufficient to permit the above-mentioned heat exchange between the preconcentrators 22 and 21 and between the extractive column 23 and the preconcentrator 22. Typical operating pressures for the four columns are: from subatmospheric pressures to about 2 atmospheres for towers 21 and 24, between 1 and 5 atmospheres for the high-pressure preconcentrator 22, and between 5 and 12 atmospheres for the extractive column 23. In the preferred version of the invention, towers 21 and 24 operate at atmospheric pressure, tower 22 operates at about 3.2 atm., and tower 23 operates at about 9.2 atm. Another variation of the invention reduces the operating pressures throughout the process so that towers 21 and, optionally, 24 operate under vacuum, tower 22 operates at about 1.9 atm. and tower 23 operates at about 5.8 atm.

In the process illustrated in the FIG. 1, the entrainer-recovery column 24 is shown as having a water-cooled condenser 42 and not being part of the thermal integration between columns. As shown in FIG. 1 in phantom, it is also possible to increase the pressure of the entrainer-recovery column 24 so that its overhead vapors are sufficiently hot that they can be condensed in condenser-reboiler 42a used to help reboil the high-pressure preconcentrator 22. In this version of the invention, both the extractive and entrainer-recovery columns 23 and 24 are used to supply the necessary heat to the high-pressure preconcentrator 22. This arrangement also changes the heat loads on exchangers 38 and 39.

Many traditional hydrous and anhydrous ethanol separation systems employ separate beer stripping and rectifying columns. In another embodiment of the subject invention, shown in FIG. 1 in phantom, column 22 functions as a beer stripper. Column 21 remains a stripper-rectifier. The condensing overhead vapors of 22 still supply the necessary heat to 21 and tower 22 is still heated by the condensing overhead vapors of the extractive column 23. The condensed overhead stream 7 from 22 is used as a second feed via line 7a to stripper-rectifier 21 instead of being mixed with stream 5, the fraction of the original dilute feed flowing to 22 changes, streams 5 and 8 are identical, and the heat duties on 38 and 39 change, causing the upper and lower feed qualities to change and thereby affect the condenser and reboiler duties of the dehydrating tower 23. Column 24 may also be included in the heat recovery network as described above.

Figure 2:
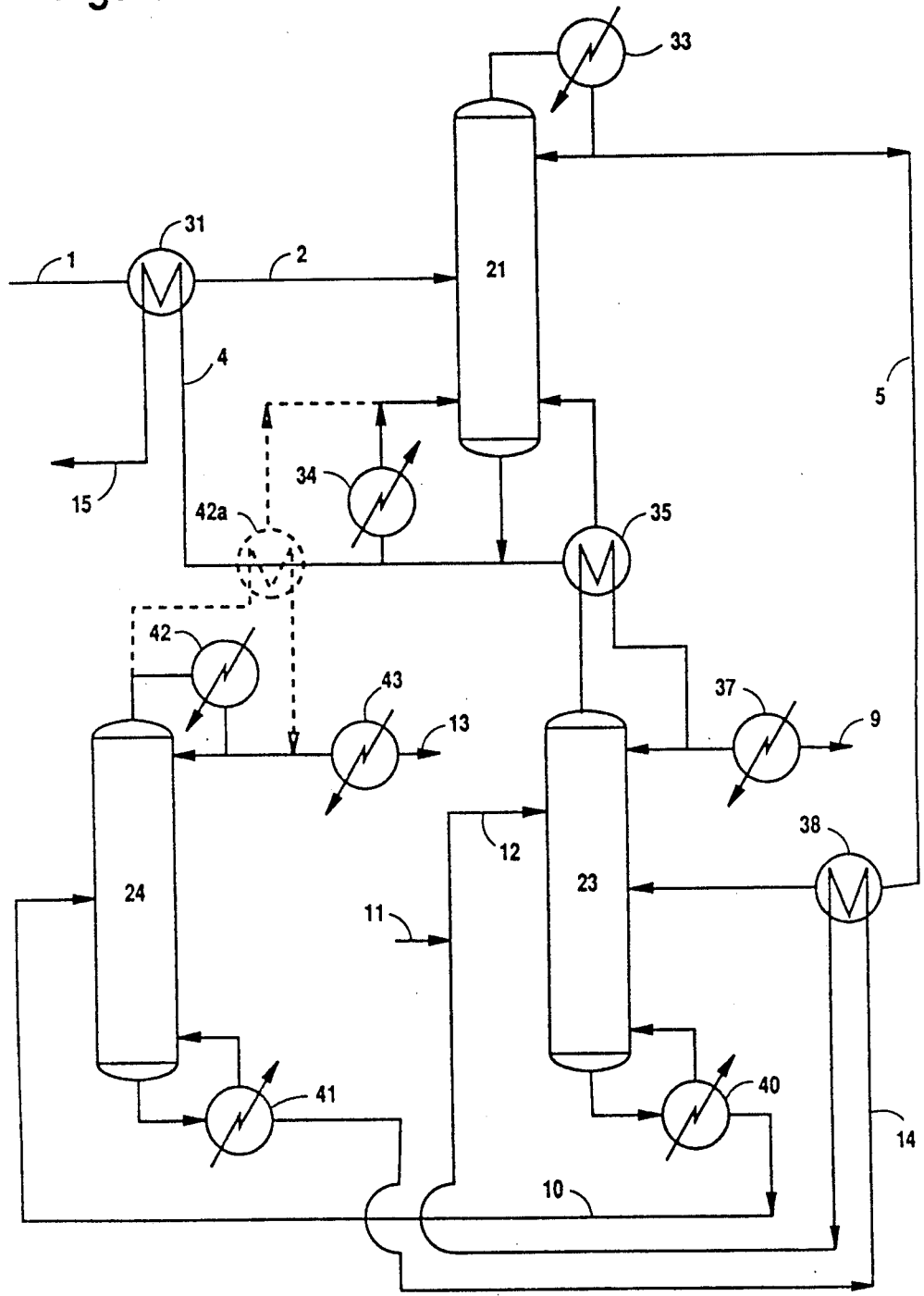
FIG. 2 is a schematic diagram of a second embodiment of the process of the subject invention.

There may be times when it is undesirable to use two preconcentrators or to operate them at elevated pressures. In such a case, substantial energy savings can still be achieved by using a different three-column, two-pressure-level, thermally-integrated extractive distillation process, as shown in FIG. 2. In FIG. 2, numbers similar to those used to describe the embodiment of FIG. 1 are used to refer to items of similar identity and function. In this second embodiment of the invention, a single preconcentrator 21 is used which operates at or below atmospheric pressure. The bottom stream 4 from this column is used as before to preheat the dilute feed 1. The extractive distillation dehydrating column 23 and, optionally indicated in phantom in FIG. 2, the entrainer-recovery column 24 may be pressurized so that their condensing overhead vapors can be used to provide part of the heat required by the preconcentrator 21. Even with condenser-boiler 42a of the entrainer-recovery column 24 included in the heat recovery network, a steam-driven reboiler 34 may be needed to satisfy the energy demand of the preconcentrator 21. Of the possible schemes for heating/cooling the feeds to the extractive and recovery columns 23 and 24, the preferred embodiment utilizes the entrainer-recycle stream 14 to heat the lower feed 5 to the extractive column 23 as hot as possible and does not heat or cool the feed 10 to the recovery column 24. For comparison with the original form of the invention, as shown in FIG. 1, this version, with the recovery column 24 included in the energy re-use network, requires 11,790 Btu/gal of anhydrous ethanol for producing a 99.8 mol% ethanol product from a 4.2 mol% feed.

In a third embodiment of the subject invention, the condensing overhead vapors of the higher pressure columns are used to generate steam or to heat some other heat transfer fluid instead of directly heating a lower-pressure column. The generated steam can then be added to the process steam supply with the lower pressure columns being heated by steam from the process utilities. Alternatively, the steam generated in the condensers of the high pressure columns can be used to reboil the lower pressure columns, i.e, the columns are indirectly thermally coupled. Steam raising will require slightly different column operating pressures than given in connection with the previous embodiments and will affect the process energy consumption accordingly.

In the various embodiments of this invention, feed ratios (i.e., the ratio of the upper feed flowrate to the lower feed flowrate in the extractive column) of between 0.4 and 4.0 are utilized. The economic optimum occurs at a feed ratio of about 0.5. However, for greater operability and controllability, a feed ratio near 1.0 may be more appropriate. For the four-column process described in FIG. 1, there is only a negligible difference in the cost and energy consumption between designs with a feed ratio of 0.5 and 1.0.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments and equivalents falling within the scope of the appended claims.

Various features of the invention are set forth in the following claims.

We claim:

1. A method for the production of substantially anhydrous ethanol comprising the steps of:
   (a) splitting a feed of a dilute ethanol in water mixture into first and second stream;
   (b) distilling said first stream in a first preconcentrating distillation column to produce a first liquid bottoms product and a first concentrated ethanol overhead vapor stream;
   (c) distilling said second stream in a second preconcentrating distillation column at an increased pressure relative to said first preconcentrating column to produce a second liquid bottoms product and a second concentrated ethanol overhead vapor stream;
   (d) preheating said first and second streams with said first and second bottoms products respectively;
   (e) condensing and combining said first and said second concentrated ethanol overhead vapor stream;
   (f) distilling said combined first and second concentrated ethanol overhead streams by extractive distillation in a third distillation column at an increased pressure relative to both preconcentrating columns to produce a third liquid bottoms product and a third overhead vapor stream;
   (g) distilling said third liquid bottoms product in a fourth distillation column to produce a fourth liquid bottoms stream and a fourth overhead vapor product;

(h) recycling said fourth liquid bottoms stream to said third distillation column as an upper feed stream;

(i) recovering heat from the condensation of said second concentrated ethanol overhead vapor stream, and using said recovered heat for heating said first preconcentrating distillation column;

(j) condensing said third overhead vapor stream to result in substantially anhydrous ethanol with heat recovered therefrom being used to heat said second preconcentrating distillation column;

(k) heating said third liquid bottoms and said fourth liquid bottoms with outside sources of heat;

(l) preheating combined first and second overhead streams from said first and second distillation columns prior to their introduction into said third distillation column by first acquiring thermal values from aid recycled fourth liquid bottoms stream and then from said third liquid bottoms product, wherein said fourth distillation column is pressurized at a range of from subatmospheric pressure to about 2 atmospheres pressure.

2. The method of claim 1 wherein said first distillation column operates in the range of from subatmospheric pressure to about 2 atmospheres pressure.

3. The method of claim 1 wherein said second distillation column operates between about 1 and about 5 atmospheres pressure.

4. The method of claim 1 wherein said third distillation column operates between about 5 and about 12 atmospheres pressure.

5. The method of claim 1 wherein said first distillation column operates at about atmospheric pressure.

6. The method of claim 1 wherein said second distillation column operates at about 3.2 atmospheres.

7. The method of claim 1 wherein said third distillation column operates at about 9.2 atmospheres.

8. The method of claim 1 wherein said fourth distillation column operates at about atmospheric pressure.

9. The method of claim 1 wherein said first distillation column operates under vacuum.

10. The method of claim 1 wherein said second distillation column operates at about 1.9 atmospheres.

11. The method of claim 1 wherein said third distillation column operates at about 5.8 atmospheres.

12. The method of claim 1 wherein said fourth distillation column operates under subatmospheric pressure.

13. The method of claim 1 wherein said fourth overhead vapors are used to help heat said second distillation column.

14. The method of claim 1 wherein said second distillation column functions as a beer stripper and said second overhead stream becomes a second feed stream to said first distillation column.

15. A method for the production of substantially anhydrous ethanol comprising the steps of:

(a) distilling a dilute aqueous ethanol mixture in a first distillation column and producing a first liquid bottoms product and a first concentrated ethanol overhead vapor stream which is then condensed;

(b) preheating said dilute aqueous ethanol mixture by heat exchange with said first liquid bottoms product;

(c) separating said first condensed concentrated ethanol overhead stream by extractive distillation in a second distillation column at an increased pressure relative to said first distillation column to produce a second liquid bottoms stream and a second overhead vapor product;

(d) distilling said second liquid bottoms stream in a third distillation column to produce a third liquid bottoms stream and a third overhead vapor product;

(e) recycling said third liquid bottoms stream to said second distillation column;

(f) condensing said second overhead vapor product to obtain a substantially anhydrous ethanol;

(g) partially heating said first distillation column with heat obtained from condensing said second overhead vapor product;

(h) providing the balance of the heating of said first distillation column with ann outside source of heat;

(i) heating said second and third distillation columns by outside sources of heat;

(j) heating said first concentrated ethanol overhead stream condensed from said first distillation column prior to its introduction into said second distillation column with heat from said recycled third liquid bottoms stream, wherein said third distillation column is pressurized at a range of from subatmospheric pressure to about 2 atmospheres pressure.

16. The method of claim 15 wherein said first distillation column operates in the range of from subatmospheric pressure to about 2 atmospheres pressure.

17. The method of claim 15 wherein said second distillation column operates between about 1 and about 5 atmospheres pressure.

18. The method of claim 15 wherein said first distillation column operates at about atmospheric pressure.

19. The method of claim 15 wherein said second distillation column operates at about 3.2 atmospheres.

20. The method of claim 15 wherein said third distillation,column operates at about atmospheric pressure.

21. The method of claim 15 wherein said first distillation column operates under vacuum.

22. The method of claim 15 wherein said second distillation column operates at about 1.9 atmospheres.

23. The method of claim 15 wherein said third distillation column operates under subatmospheric pressure.

24. The method of claim 15 wherein said third overhead vapors are used to help heat said first distillation column.

* * * * *

UNITED STATES PATENT AND TRADEMARK OFFICE
CERTIFICATE OF CORRECTION

PATENT NO. : 5,035,776                                    Page 1 of 2

DATED : July 30, 1991

INVENTOR(S) : Knapp, et al.

It is certified that error appears in the above-identified patent and that said Letters Patent is hereby corrected as shown below:

Column 2, Line 26, "preheat dilute feed" should be --preheat the dilute feed--.

Column 2, Line 40, "U.S. Patent No. 4,422,903 which reduces" should be --U.S. Patent No. 4,422,903 reduces--.

Column 4, Line 57, "bear stripper" should be --beer stripper--.

Column 5, Line 7, "stream B" should be --stream 8--.

Column 5, Line 67, "directed too" should be --directed to--.

Column 6, Line 6, ", the fuel oils," should be --, the fusel oils,--.

Column 8, Line 46, "second stream;" should be --second streams;--.

UNITED STATES PATENT AND TRADEMARK OFFICE
CERTIFICATE OF CORRECTION

PATENT NO. : 5,035,776

DATED : July 30, 1991

INVENTOR(S) : Knapp, et al.

It is certified that error appears in the above-identified patent and that said Letters Patent is hereby corrected as shown below:

Col. 10, line 30, "stream condensed" should be --condensed stream--

Signed and Sealed this

Twenty-second Day of December, 1992

*Attest:*

*Attesting Officer*

DOUGLAS B. COMER

*Acting Commissioner of Patents and Trademarks*